United States Patent [19]
McClain

[11] Patent Number: 5,460,192
[45] Date of Patent: Oct. 24, 1995

[54] APPARATUS FOR APPLYING SUNTANNING LOTION

[76] Inventor: Edward T. McClain, 416 Park Place Ave., Bradley Beach, N.J. 07720

[21] Appl. No.: 161,803

[22] Filed: Dec. 6, 1993

[51] Int. Cl.⁶ .................................................. A61H 33/06
[52] U.S. Cl. .......................... 132/333; 601/160; 600/21; 4/525; 4/597; 4/603; 119/159
[58] Field of Search .................................... 132/320, 333; 4/524, 528, 531, 596, 597, 602, 603, 611, 612, 615, 616, 525; 119/158, 159, 160; 604/19; 601/154, 155, 156, 160; 600/21

[56] References Cited

U.S. PATENT DOCUMENTS

| | | | |
|---|---|---|---|
| 624,420 | 5/1899 | Atwater et al. | 4/524 |
| 871,074 | 11/1907 | Stockton | 4/524 |
| 3,009,165 | 11/1961 | Washam et al. | 4/524 |
| 3,396,411 | 8/1968 | Vieceli | 4/525 |
| 4,020,796 | 5/1977 | Grifa | 119/158 |
| 4,056,078 | 11/1977 | Blafford et al. | 119/158 |
| 4,083,328 | 4/1978 | Baker | 119/158 |
| 4,196,479 | 4/1980 | Geisler | 4/524 |
| 4,425,672 | 1/1984 | Johnson et al. | 4/596 |
| 4,765,542 | 8/1988 | Carlson | 4/602 |
| 4,862,526 | 9/1989 | Berger | 4/525 |
| 5,259,339 | 11/1993 | McLaughlin | 119/158 |

FOREIGN PATENT DOCUMENTS 224165  8/1991  United Kingdom ..................... 4/531

Primary Examiner—John G. Weiss
Attorney, Agent, or Firm—Martin J. Spellman, Jr.

[57] ABSTRACT

An apparatus for applying suntan lotion including a liquid tight enclosure of generally cylindrical shape. The upper wall portions are tilted inwardly to form a central neck enclosure. A door in side walls of the enclosure is spring biased to the closed position. Suntan lotion is pumped through vertically spaced nozzles from a pump and supply source exterior of the enclosure. The pump is controlled by a revenue token device outside the apparatus with a time delay arrangement allowing the user to deposit tokens, enter the enclosure, and close the door before the lotion starts spraying for a predetermined time.

1 Claim, 5 Drawing Sheets

APPARATUS FOR APPLYING SUNTANNING LOTION

BACKGROUND OF THE INVENTION

1. Field of the Invention

This invention is concerned with apparatus for conveniently and neatly applying suntan lotion to the entire body, automatically and efficiently. The apparatus uniformly distributes the lotion over the skin surface of the user in a few seconds. The term suntan lotion is meant to include emollient forms of conventional tanning lotion and the now widely used blocking screen lotions. The latter prevent burning and tanning of the skin with the resulting damage to the skin cells which lead not only to painful burns, and in some cases blistering, but often to long term deleterious effects of the skin.

It is now well known that undue exposure to the ultraviolet rays of the sun greatly increases the probability of the individual developing skin cancer, often years subsequent to the exposure to the burning rays of the sun.

The present protective lotions currently are applied by individual users usually from a jar or a squeeze tube container either in globs on a skin surface or in the palm of the hand and the lotion subsequently spread on other parts of the body. This generally results in very uneven application, often missing certain hard to reach areas of the skin, as well as requiring the wasteful dispensing of multiple portions of the lotion during the application process. In addition, it is often applied on the beach and users are exposed to getting sand stuck to their hands or other portions of the body where the lotion is applied and dries on the skin. This causes great annoyance and discomfort.

On occasion, individuals forget to bring lotion with them and either are forced to borrow from a companion or to risk a severe burn and exposure to dangerous ultra violet solar rays for that day.

The apparatus of the present invention is designed to be located at the beach or other suntanning areas to provide a way of uniformly dispensing sun tan lotion by spraying it evenly on the body of the user in a rapid, convenient, and inexpensive manner. The apparatus most often would be controlled by a coin operated or bill actuator installed on or adjacent the apparatus.

The apparatus comprises a specifically designed enclosure for the user's body, except for the head, having lotion dispensing spray nozzles appropriately located and mounted against the inner walls of the apparatus, a pump for supplying lotion to the enclosure through distribution pipes and spray heads, a reservoir for the lotion, and associated controller and motor.

2. Prior Art

There is no apparatus presently on the market or known that is specifically designed for applying suntan lotion or sun tan blocking lotion uniformly to the skin of the user.

Of remote background interest are U.S. Pat. No. 157,846, Leslie and U.S. Pat. No. 582,639, Gray which disclose cabinets which enclose the human body for purposes of applying vapor or steam baths. U.S. Pat. No. 3,590,398, Jetter and U.S. Pat. No. 5,216,763, Grenier discloses portable shower arrangements wherein the person using the device stands in the inside the enclosure while shower water is supplied through appropriate dispensing nozzles at the upper end of the device.

U.S. Pat. No. 4,862,526, Berger discloses an enclosure wherein vapors contact the body as the user sits within the enclosure.

SUMMARY OF THE INVENTION

This invention comprises an apparatus for uniformly applying suntan lotion to the user's torso and limbs by a token operated mechanism. The apparatus comprises a base platform having a drain aperture, a recess for retaining a grid on which the user stands, and means for securing the enclosure portion of the apparatus and supporting the associated pump, storage containers, motor and controls which are generally stored exteriorly of the apparatus enclosure.

The enclosure is generally of an upright cylindrical shape with one open end secured to the base and the top end tapering inwardly to a neck enclosure for the user at the top.

One portion of the exterior walls of the container serves as a closely fitting door opening. The door is provided with spring biased hinges and preferably is mounted on a piano type of hinge that is vertically oriented.

Multiple spray heads are located approximately shoulder height, intermediately and in the area of the legs and supplied by distribution pipes.

The distribution lines join a supply pipe to a pump, supply reservoir for the lotion, a motor to drive the pump, and associated controls that are connected to controls utilized by the user that are mounted on the exterior of the enclosure nearby the door.

A suitable pump is one typically used for spray painting such as one operating at pressures up to 2,500 p.s.i. and driven by ½ horsepower 60 Hz motor. The pressure utilized is adjusted according to viscosity of the lotion to spray a fine spray of droplets.

The floor of the base is tilted towards a drain hole so that the excess lotion may drain out and the interior of the enclosure may be readily flushed out with water and/or other cleaning fluid whenever cleaning is necessary. It is not required to clean the device very often because the orientation of the distribution nozzles assures that most of the lotion is applied to the user's torso and limbs and that there is very little overspray. In use, any excess applied to user's body may be wiped off with the user's hands and applied to user's face and ears, neck and the like which are not within the spraying field.

BRIEF DESCRIPTION OF THE DRAWING

In the accompanying drawing which forms of a part of the specification.

ILLUSTRATIVE SPECIFIC EMBODIMENT

Figure 1:
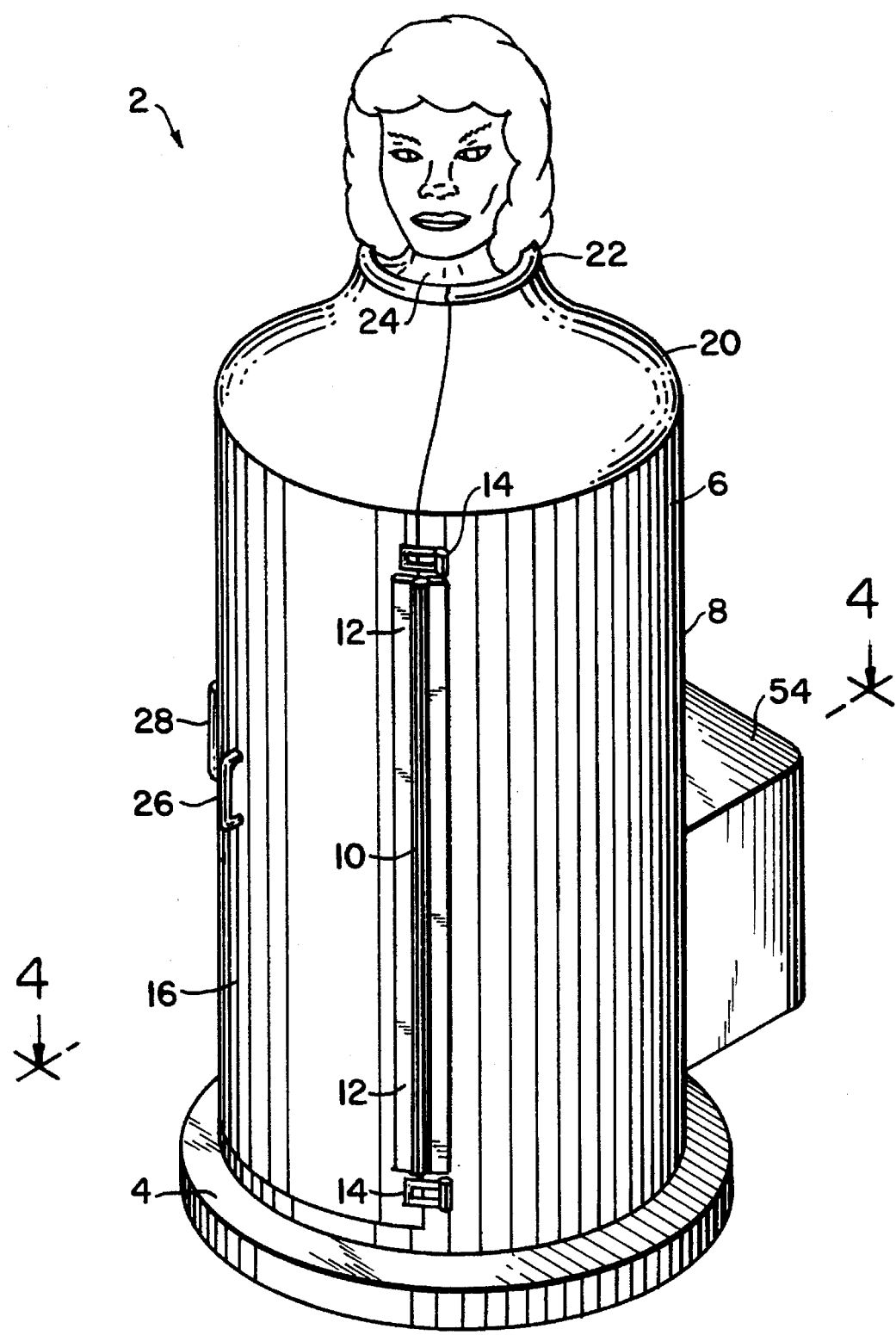
FIG. 1 is a perspective view of the apparatus with a user within the apparatus and the door of the apparatus closed.
Figure 2:
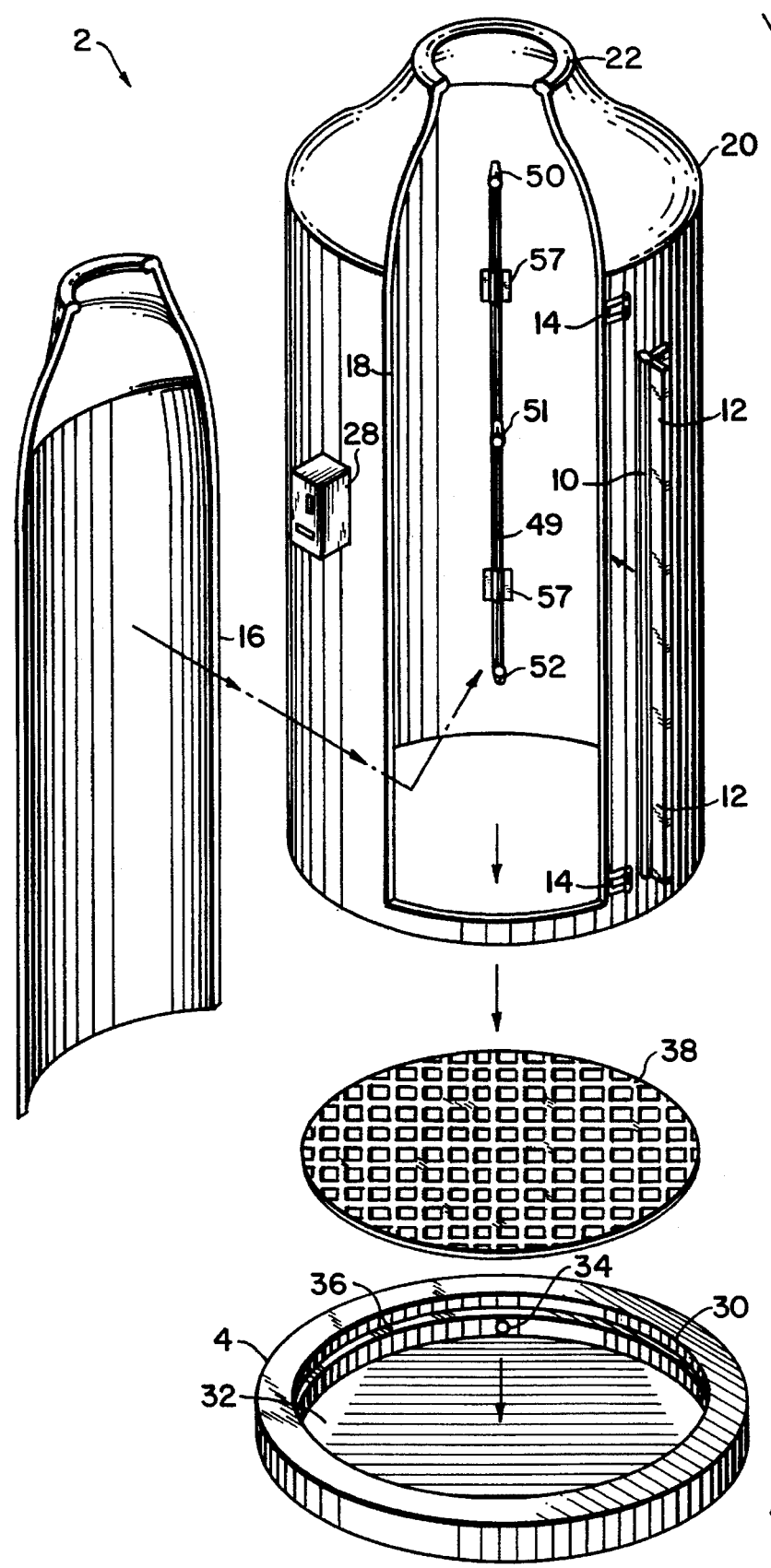
FIG. 2 is a partially expanded view of the apparatus showing the interior and the assembly of the door access panel base and drain grate.

Referring to the accompanying drawing, the apparatus of the present invention is indicated generally by the numeral 2. The apparatus 2 comprises a base 4, a cylindrical enclosure 6 having sides 8 and swinging door 16 with handle 26.

The door 16 is mounted on piano hinge 10 having leaves 12 and a pair of spring biased tabs 14 urging the door 16 to a closed position. The door 16 has a beveled edge 18 and the opening for the door 16 a recess 17 to help provide a secure seal when the door 16 is closed. The upper portions of the sides 8 are slanted in as shown at 20. The collar flange opening 22 has the interior rolled smoothly to provide a comfortable surface for the neck of the user 24. The diameter of 6 is approximately 3 feet and the height 4 ½ to 5 feet. Tall users may crouch slightly as necessary.

Figure 3:
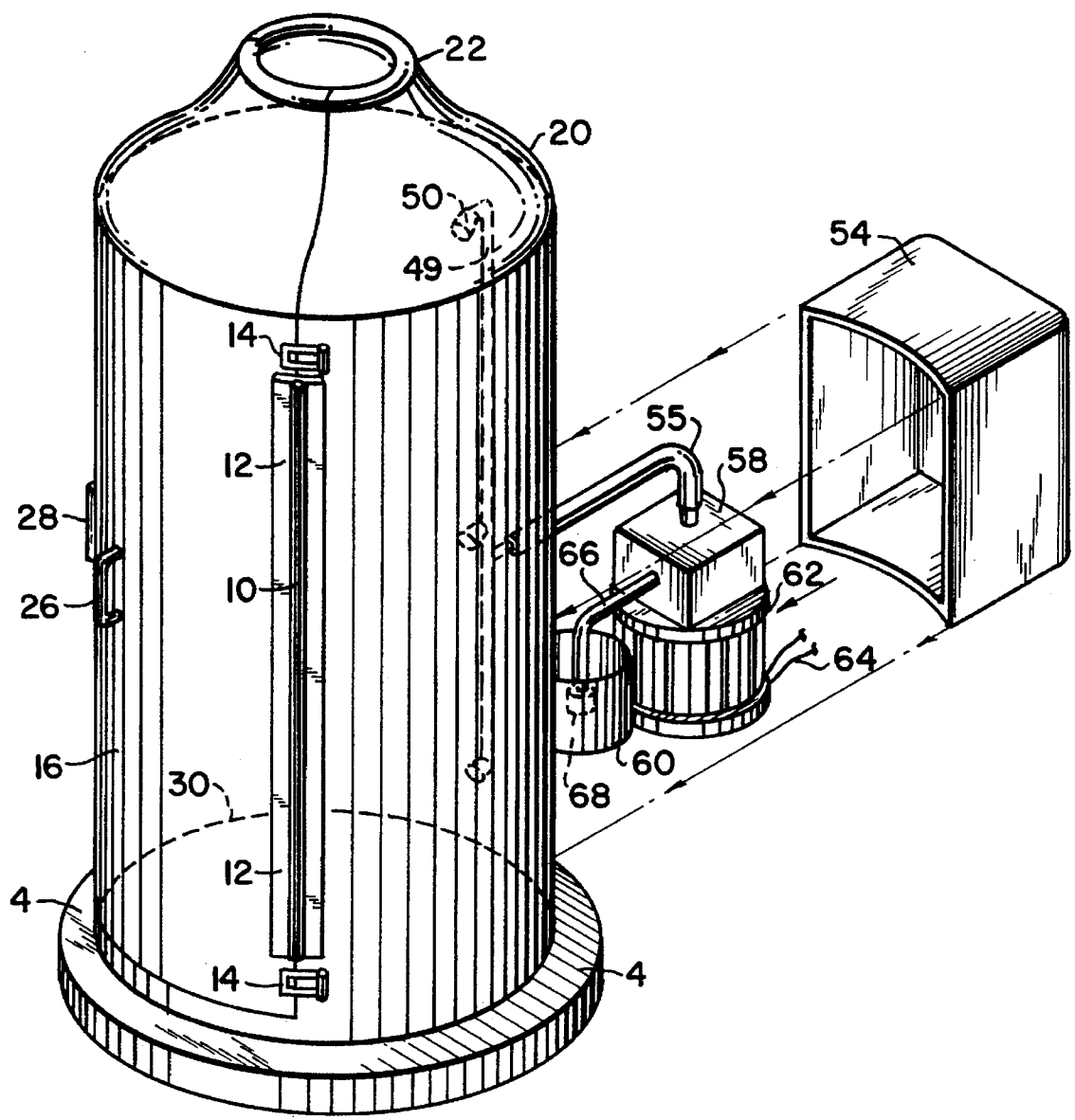
FIG. 3 is also a partially exploded view of the apparatus showing the door enclosed and the equipment panel removed showing the distribution pipes, reservoir, pump and motor components.
Figure 4:
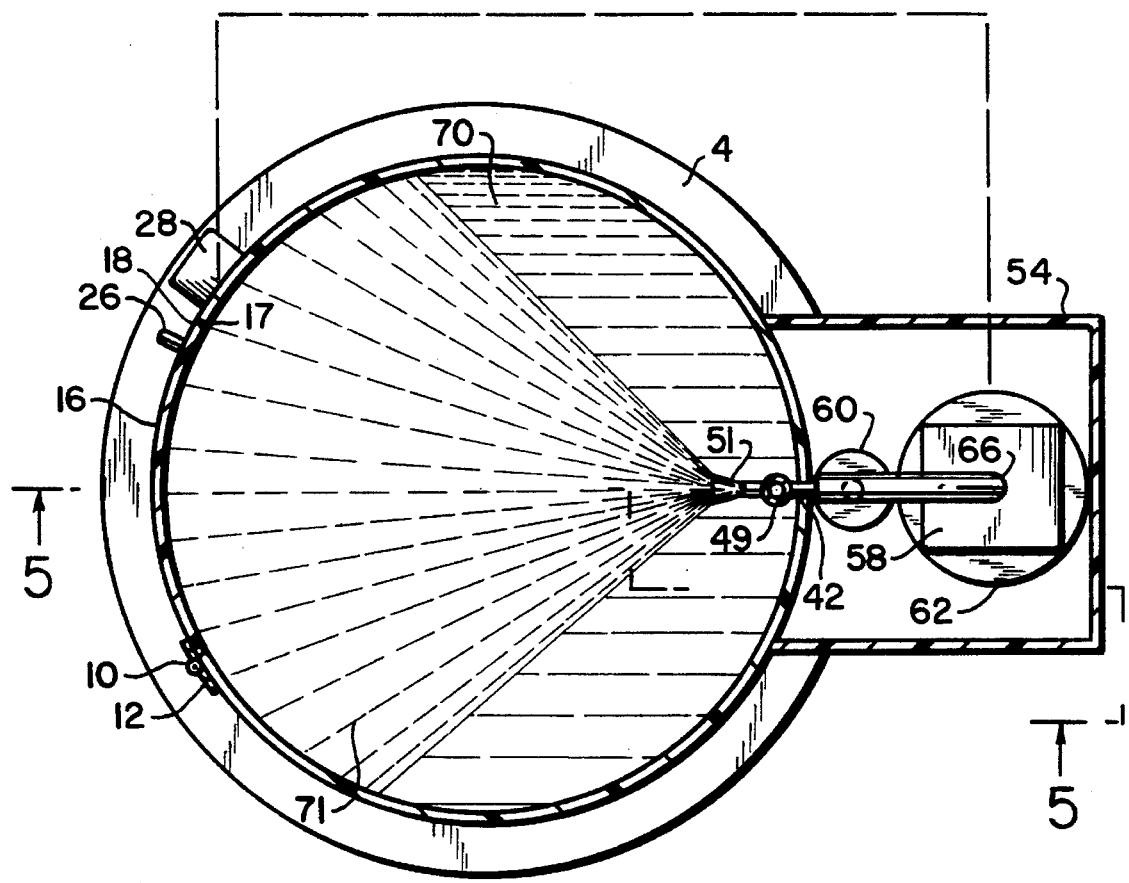
FIG. 4 is a sectional view along lines 4—4 of FIG. 1.
Figure 5:
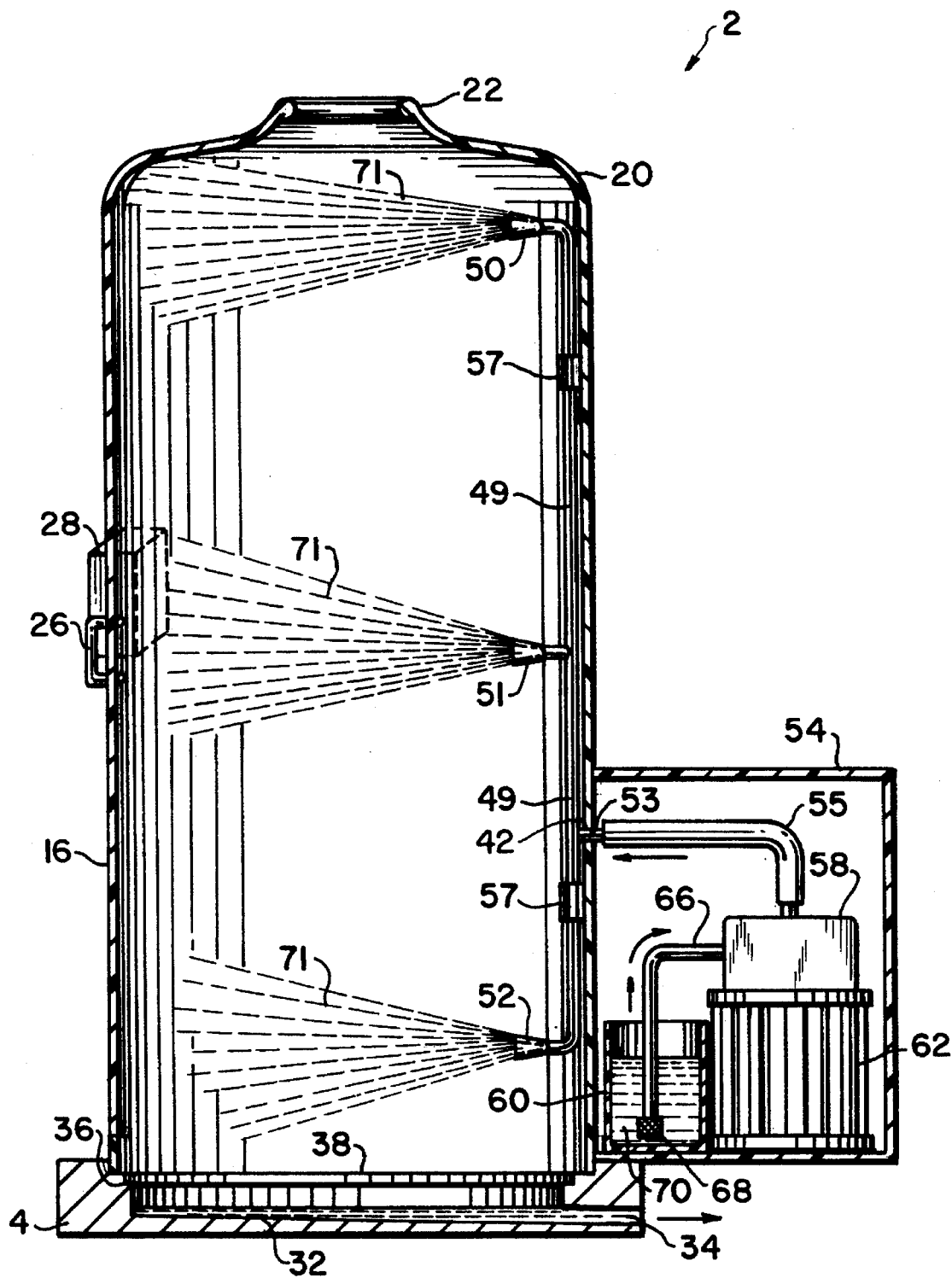
FIG. 5 is a sectional view along lines 5—5 of FIG. 4.

The base 4 has a recess 30 formed therein and the bottom 32 is provided at the side with drain hole 34 for emptying out cleansing water or other liquids when the device is cleaned out. A ledge 36 formed in the recess 30 in the base 4 provides a mounting for the grating 38 on which the user 24 stands. The interior of the sides has a pipe 49 secured by brackets 57 thereto. At the top, middle and the bottom of pipe 49 supply nozzles 50, 51 and 52 respectively are in flow connection thereto. The supply line 49 and the nozzles 50, 51 and 52 are mounted as shown more particularly in FIG. 3. Conduit 55 from pump 58 goes through opening 42 in wall 8 and joins pipe 49. The pump 58, supply reservoir 60 for the lotion 70 and an electric motor 62 to drive the pump 58 are all enclosed by cover 54. The lotion 70 passes through a filter 68 before entering the supply pipe 66 leading to pump 58. Electrical lines 64 (FIG. 3) lead to the power supply which is controlled by a token operated switching mechanism 28 of known type. The lines connecting control unit 28 and power supply (not illustrated) are indicated schematically by the dashed line in FIG. 4.

When the user 24 desires to use the apparatus 2 he or she deposits the appropriate revenue into the token receptacle mechanism 28 and steps inside the enclosure 6. The token receptacle control 28 provides a 10 to 15 second delay to allow the user to locate within the enclosure 6, then cause the pump 62 to operate for 10 to 20 seconds or whatever appropriate time is selected that is predetermined in order to apply the lotion to the user. The time selected will vary with the specific lotion utilized. The pump 58 forces the lotion 70 out the nozzles 50, 51 and 52 and the spray 71 of droplets is emitted. The user 24 turns around in the enclosure 6 to allow the lotion 70 to be evenly distributed over his limbs and torso. When the pump 58 automatically turns off, after a preselected time, the user 24 exits the enclosure 6 and then can use the excess lotion 70 on his or her limbs and torso to apply to the face and neck with the palms of his or her hands.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. Apparatus for applying suntan lotion to a human body comprising a liquid tight generally upright cylindrically shaped enclosure having side walls, a top end of said cylindrically shaped enclosure tapering inwardly to a neck enclosure for a user, a base for said cylindrically shaped enclosure having a drain aperture therein, a grate mounted in a recess of said base, a door in said side wall of said cylindrically shaped enclosure spring biased to a closed position, a plurality of discrete liquid spray nozzles vertically aligned disposed about an interior of said cylindrically shaped enclosure at different heights and in flow communication with lotion distribution pipes, said lotion distribution pipes in flow communication with a pump for pumping lotion from a supply reservoir associated with said pump, an electric motor driving said pump, and control means operating said pump motor a predetermined length of time when actuated by a token operated control means, said control means providing a delay period of time from when revenue is deposited to starting operation of said pump.

* * * * *